United States Patent [19]

Larsonneur

[11] Patent Number: 5,252,374

[45] Date of Patent: Oct. 12, 1993

[54] UNDERPAD FOR INCONTINENT PATIENTS

[75] Inventor: Lionel M. Larsonneur, Pomona, Calif.

[73] Assignee: Paper-Pak Products, Inc., La Verne, Calif.

[21] Appl. No.: 837,820

[22] Filed: Feb. 18, 1992

[51] Int. Cl.⁵ .............................................. B32B 3/14
[52] U.S. Cl. ...................................... 428/77; 428/68;
428/74; 428/76; 428/153; 428/154; 5/484;
5/487; 5/502; 604/368; 604/378; 604/379;
604/384; 604/385.1
[58] Field of Search .............. 428/68, 77, 76, 74,
428/153, 154, 152, 184, 186; 604/385.1, 384,
379, 358, 378, 368; 5/484, 502, 487

[56] References Cited

U.S. PATENT DOCUMENTS

| 2,707,289 | 5/1955 | Taggart | 5/484 |
| 3,848,599 | 11/1974 | Schaar | 604/385.1 |
| 3,903,889 | 9/1975 | Torr | 428/153 |
| 4,097,943 | 7/1978 | O'Connell | 5/484 |
| 4,643,729 | 2/1987 | Gegelys | 604/378 |
| 4,753,645 | 6/1988 | Johnson | 604/378 |
| 4,960,477 | 10/1990 | Mesek | 604/378 |
| 5,037,409 | 8/1991 | Chen | 604/358 |

FOREIGN PATENT DOCUMENTS 2636899 3/1977 Fed. Rep. of Germany ...... 604/378

Primary Examiner—Ellis P. Robinson
Assistant Examiner—Nasser Ahmad
Attorney, Agent, or Firm—Henry M. Bissell

[57] ABSTRACT

An absorbent underpad for use on an article of bedding includes a liquid impervious backing sheet, a liquid permeable upper facing sheet adhered to the backing sheet about the edges thereof, and an interior absorbent pad combination comprising upper and lower tissue layers generally coextensive with the boundarees of the underpad, a pair of spatially separated barrier strips formed of super-absorbent material between the tissue layers, and a non-woven transfer layer along the central region of the upper tissue layer adjacent the upper facing sheet. The plies of the tissue layer are formed with a crepe-like irregular surface oriented to develop a wicking action directed along the layers in a transverse direction, toward the absorbent barrier strips.

24 Claims, 2 Drawing Sheets

UNDERPAD FOR INCONTINENT PATIENTS

BACKGROUND OF THE INVENTION

1. Field of the Invention

This invention relates to absorbent pads and, more particularly, to such pads which are designed for protecting bedding against soiling by incontinent patients, principally for use on beds in hospitals, nursing homes and the like.

2. Description of the Related Art

Various approaches to solving the problem of protecting bedding from incontinent patients are known in the prior art. For example, rubber sheets have been used, usually placed over a mattress and underneath the lower cloth sheet on a bed. While they serve the primary purpose of protecting the mattress, they are extremely uncomfortable for the patient.

Hospital underpads have been developed as a preferable alternative to the rubber sheet. Since these underpads are more comfortable for the patient to lie on in direct contact with, they are placed on top of the lower sheet, thereby protecting it as well as the mattress. One type of hospital underpad which has long been on the market comprises a plurality of soft, fibrous tissue layers backed by a soft, waterproof polyethylene backing layer. The four edges of the backing layer are turned and/or sealed. The absorbent tissue layers are uniform and lump free, and provide maximum absorbency and dispersion of liquid. Runoff or leakage is prevented by virtue of the sealed edges. Instead of the fibrous tissue layers, some underpads are formed of packed tissue or fluffed wood pulp. These hospital underpads are provided in appropriate sizes to cover the vulnerable area underneath the patient and are available in individual packs for ease of stocking and handling.

The turned edges of the hospital underpads just described present an upper surface of polyethylene or polypropylene backing which frequently comes in contact with the patient's skin where it can create "hot spots" or cause skin breakdown, resulting in bedsores which sometimes lead to a type of cancer. Bedsores are a serious problem with longer term bedridden patients, particularly the elderly. Statistics on the subject indicate that some 30,000 patients die of complications from bedsores every year. The problems are exacerbated with underpads that do not have the liquid absorbent capacity needed for comfort or which are not changed often enough.

Some of these hospital underpads are equipped with adhesive strips of pressure-sensitive tape or plastic melt or the like on the exposed surface of the backing layer in order to hold the underpad in place underneath the patient without bunching up or displacement from the desired position of maximum effectiveness. In some examples of the prior art, the bottommost absorbent layer is adhesively laminated to the impervious backing sheet.

In an effort to improve the absorbent capability of hospital underpads, variations have been developed in which wood pulp is interspersed with the soft fibrous tissue layers. Sometimes, a super-absorbent powder is mixed with the wood pulp in homogeneous distribution within the pad. Unfortunately, if such pads are left with a patient too long, the filling with liquid develops a slimy combination of the wood pulp, super-absorbent powder and urine that is particularly likely to cause skin breakdown if left in contact with the patient's body. Thus such arrangements, even though more absorbent, still do not provide a completely satisfactory answer to the problem of developing an absorbent underpad for incontinent patients. It is desirable, therefore, to provide a novel construction for hospital underpads which increases the absorbent capacity of the product to a significant extent over that of presently known absorbent underpads.

SUMMARY OF THE INVENTION

In brief, arrangements in accordance with the present invention provide an absorbent underpad for use on beds in hospitals, nursing homes, and the like which develops an improved capability for liquid absorption by virtue of its novel structural configuration as well as its use of particular absorbent materials. The underpad basically comprises an uppermost layer, a bottom or backing layer and a plurality of intermediate layers to establish the liquid absorbent capability of the pad. In one preferred embodiment, the backing layer is a thin sheet of impervious polypropylene plastic, as is the case with presently known underpads. However, the edges are not folded over on top of the uppermost layer of the pad but instead are adhered along the underside of the uppermost layer by separate narrow lines of glue extending along the two side edges of the pad between the two outermost layers.

The upper layer of the underpad is a porous layer, permeable to liquid, of open weave, spun-bonded sheet, hydrophobic material, preferably of polypropylene facing. Directly underneath that is a transfer layer of non-woven polyester hydrophilic material which allows liquid to pass through readily into the inner layers of the pad but impedes any passage of the liquid in the opposite direction. Next, along the inner side of the transfer layer, is an upper layer of tissue. The upper surface of the transfer layer, being next to the uppermost layer, tends to draw liquid through the open weave. However, the lower surface of the transfer layer, being next to the upper tissue layer, does not exhibit the same tendency, thus accounting for the directional transfer of liquid therethrough.

The upper tissue layer comprises a plurality of plies of thin, soft, fibrous tissue which are formed together to constitute the upper absorbent tissue layer next to the transfer layer. This combination of the one-way liquid passage effected by the transfer layer and the absorbency of the adjacent tissue layer achieves the very beneficial result that the pad develops a feeling of dryness along its upper surface, even though it may have only recently been wet.

Beneath the upper tissue layer and extending lengthwise of the underpad is, preferably, a pair of spatially separated strips of laminated super-absorbent polymer powder material. These laminated strips, preferably about 2" wide and extending virtually the full length of the pad, serve as barriers to any liquid which passes by capillary action outward from the central region of the pad or inward from the side edge of the pad and complete the absorption of the liquid in the side areas of the pad which are generally outside the region where the patient's body rests. On the underside of these barrier strips is a lower tissue layer, essentially identical to the upper tissue layer.

The upper and lower tissue layers are formed of as many as ten plies of highly absorbent tissue, fabricated with a crepe construction which is aligned transversely of the pad to establish a preferential direction for the capillary action for liquid which is absorbed within the tissue layers. Together with the barrier strips between them, the upper and lower tissue layers form a sort of sandwich. The combination of the transversely directed wicking action in conjunction with the super-absorbent barrier strips along the sides of the pad serves to direct the liquid away from the central region of the pad, the area where the patient's body is most likely situated, to near the edges where the liquid is absorbed. Thus the central region of the pad is kept reasonably dry, even though the pad may have a substantial amount of liquid within it, and so enhancing the comfort of the patient who is lying on the pad and within the bed. As an added aspect of comfort to the patient, the removal of liquid from the center makes the upper facing layer feel dry to the touch.

The barrier strips are of laminated absorbent material, comprising upper and lower thin layers of absorbent tissue with super-absorbent powder distributed in a generally random fashion between them. These barrier strips are available commercially from Gelock, Inc., Pine Lake Industrial Park, Dunbridge, Ohio 43414.

Absorbent underpads of the type involved in the present invention are commonly made in a range of sizes which may be 17-½×24", 23×24" or 23×36". In one particular embodiment of an underpad in accordance with the present invention, the pad is approximately 29½"square. About ½" in from each side edge of the pad is a glue line extending the length of the pad, sometimes referred to as the "machine direction", which adheres the side edges of the pad together between the upper spun-bonded permeable sheet and the lower polypropylene plastic impervious backing layer. The internal components of the pad—the upper and lower tissue layers with the side barrier strips which make up the sandwich construction to direct the liquid flow within the pad—are closely contiguous to the side edge glue lines but terminate short of the top and bottom edges of the pad by about 2½" on each upper and lower edge. The tissue layers extend to within approximately ½" of the side edges while the intermediate barrier strips are spaced about three or four inches therefrom. This arrangement provides a region where the external surface layers are loosely and somewhat intermittently adhered together with sufficient space in the inner pad region to provide some leeway at the ends for the cutting blade as it separates the individual pads during fabrication. It will be understood that the pads are formed from rolls of the respective layer elements on a production line.

The upper, or inner, surface of the polypropylene backing layer is sticky, and this is effective to accomplish the adherence of the upper spun-bonded facing layer to the polypropylene backing layer at the longitudinal ends of the pad where these two layers come in contact. The stickiness of the inner surface of the polypropylene backing layer is accomplished by spraying glue fibers on the upper surface of the backing sheet at intervals along the production line corresponding to the interpad area where the slitting will occur. There is a slight overlap of the sticky surface with the location of the tissue layers within the pad so that the ends of the bottom tissue ply also adhere to the surface, thereby serving to hold the internal components of the pad in position.

In a second preferred embodiment of the invention, the impervious backing layer is replaced by a non-woven, spun-bonded sheet which has a certain degree of porosity. In both embodiments, the upper facing layer comprise ½ ounce spun-bonded material which is sprayed with a surfactant that facilitates the passage of liquid therethrough. The backing layer of the second embodiment, however, is formed of heavier 1¼ ounce spun-bonded material without the surfactant treatment. This is almost impervious to water but is permeable to air. The second embodiment of my invention finds particular application in use with air beds, such as are used for burn victims, patients with ulcerated skin, etc. These air beds have a core of beads or sand which permit air at a slightly elevated pressure to flow through them from the bottom up, thereby assisting in drying the skin. The porosity of the heavier non-woven backing layer without any surfactant treatment is such that the pressurized air passes through, but only the slightest bit of moisture can penetrate the backing layer from the upper side. This serves to prevent any "strike through" of moisture from the pad to the bed. This embodiment is typically slightly longer than the first embodiment described hereinabove. Dimensions of this underpad are preferably 29½" wide by 35½" long with the lengths of the individual components of the underpad being adjusted accordingly.

During assembly of the constituent components of the underpad as it proceeds along the production line, the interior laminations of the upper and lower tissue layers with the side strip barriers between them are loosely secured together by longitudinal lines of pressure bond stitching spaced approximately two to four inches apart. As is known in the art, this pressure bond stitching is formed by running a serrated wheel under load along the tissue layers, thus penetrating and compressing them sufficiently to create the lines of pressure bonds.

The transfer layer is approximately as long as the tissue layer sandwich but is somewhat narrower, being located along the center of the pad, generally equidistant from the side edges. The width of the transfer layer is sufficient to overlap and cover the side barrier strips. In the particular 29½" square embodiment of the invention referred to hereinabove, the transfer layer is approximately 17½" wide and the side barrier strips are about 2" wide and spaced about 6" from the side edges, leaving a space between the strips of about 13½".

BRIEF DESCRIPTION OF THE DRAWING

A better understanding of the present invention may be realized from a consideration of the following detailed description, taken in conjunction with the accompanying drawing, in which.

DETAILED DESCRIPTION OF THE PREFERRED EMBODIMENTS

Figure 1:
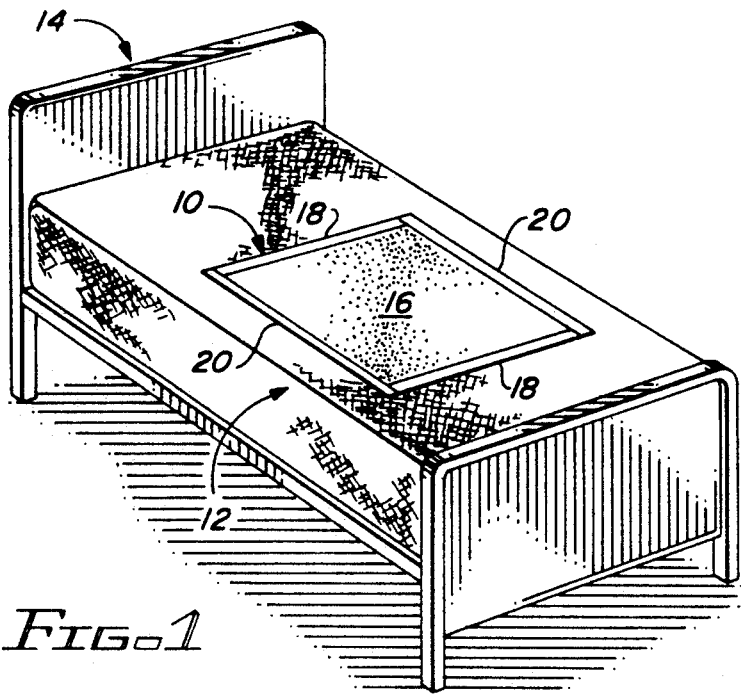
FIG 1 is a perspective view of a typical absorbent underpad of the prior art, shown in position on a bed.

As shown on FIG. 1, a conventional hospital underpad 10 of the prior art is positioned for use on the lower sheet 12 of a hospital bed 14. The underpad 10 comprises an absorbent central area 16 with sealed longitudinal edges 18 and lateral edges 20 which are formed by folding over the backing layer and sealing it along the upper edge surface of the upper sheet. This may be considered to exemplify the prior art, such as that which is the subject of the O'Connell patent 4,097,943.

Figure 2:
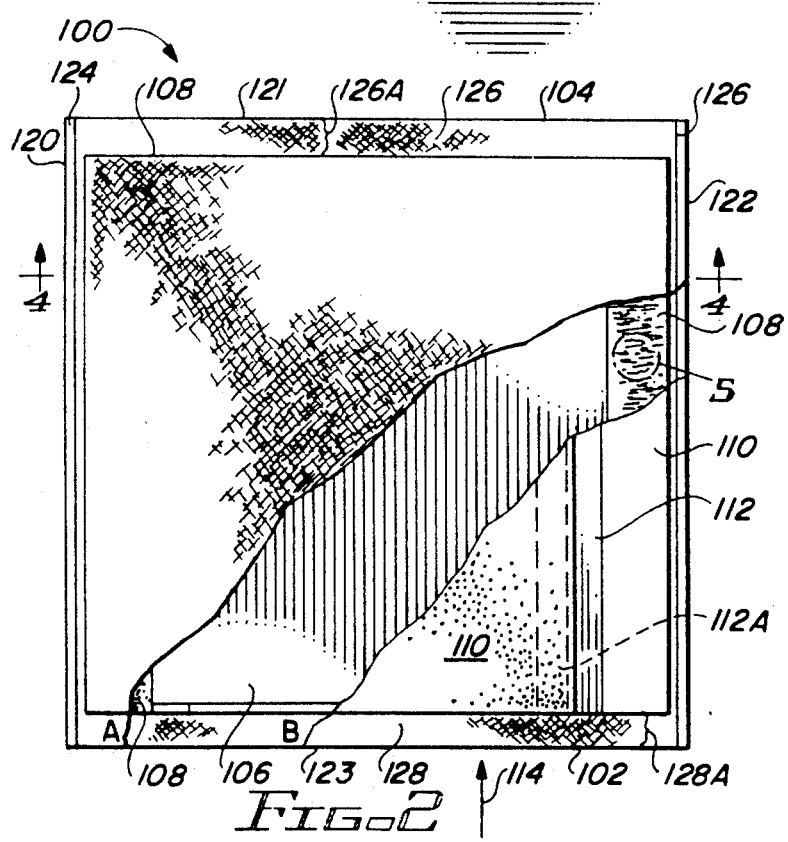
FIG. 2 is a schematic plan view, partially broken away, of one particular arrangement in accordance with the present invention.
Figure 3:
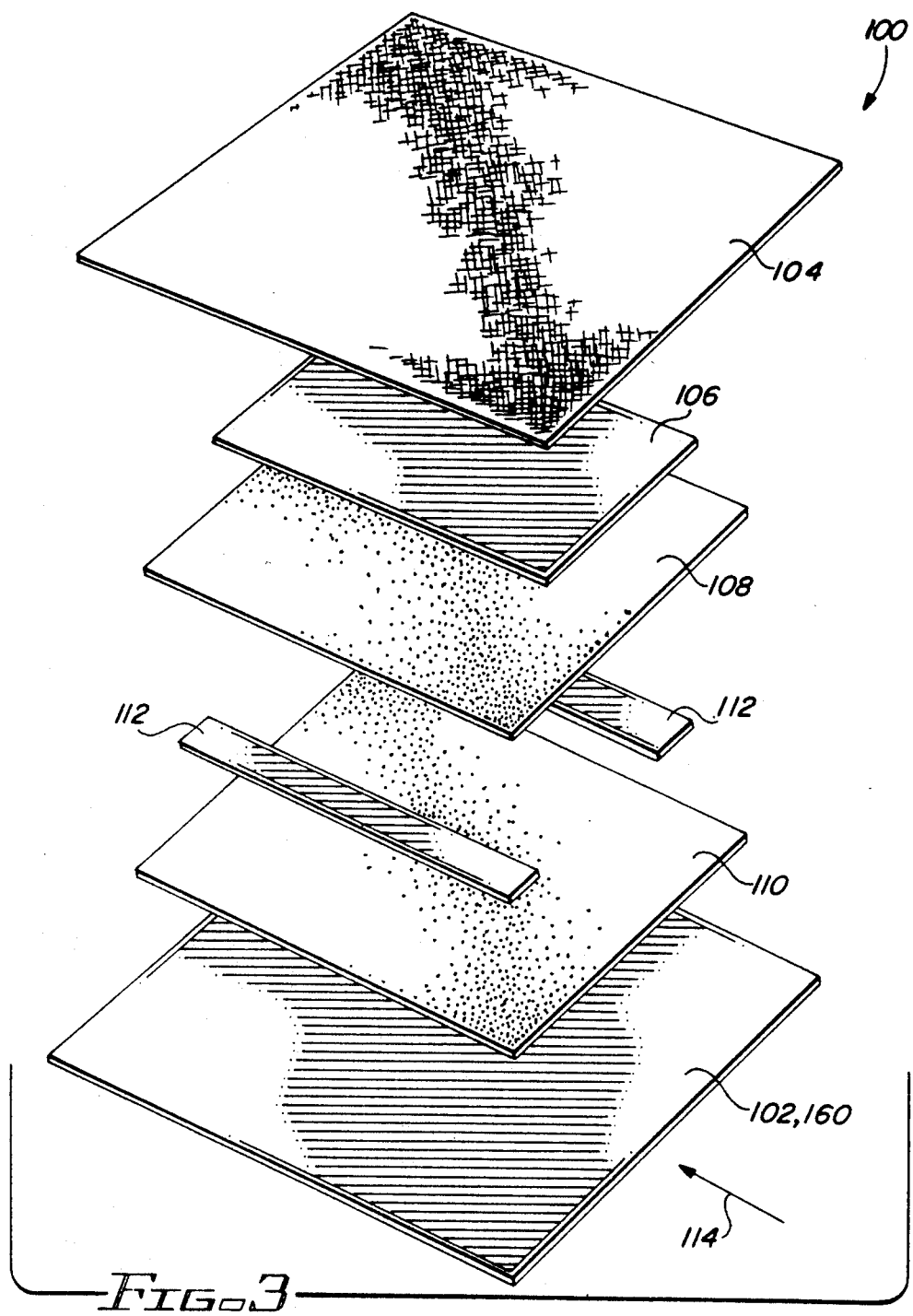
FIG. 3 is a schematic exploded view showing the various components of the arrangement of FIG. 2.

The preferred embodiments of the present invention, as best shown in the schematic views of FIG. 2 (a partially broken away plan view) and FIG. 3 (an exploded view) show an underpad 100 comprising a backing layer 102 and an upper layer 104 between which are a transfer layer 106, an upper tissue layer 108, and a lower tissue layer 110, the tissue layers being separated by a pair of spaced-apart absorbent strips 112. The arrow 114 indicates the longitudinal direction of the underpad 100. The cross hatching and other marking on the respective components in FIG. 2 is not intended to indicate any particular construction but is merely to emphasize the different individual components.

The upper spun-bonded sheet 104 is sufficiently open as to appear partially transparent, at least to the extent that the outline of the upper tissue layer 108 is discernible through it, particularly against the darker background of the blue polyethylene backing sheet 102 (see FIG. 2). The upper and lower sheets 102, 104 are secured together along the side edges 120, 122 by lines of glue 124, 126 and, at the top and bottom ends 121, 123, by the stickiness of the glue fibers sprayed on the inner surface of the backing layer 102 in the end regions 126, 128. The regions of sprayed glue fibers generally extend in the areas 126A and 128A, thereby providing a slight overlap with the tissue layers 108, 110 with the result that the lower tissue layer 110 adheres to the backing layer 102.

Figure 4:
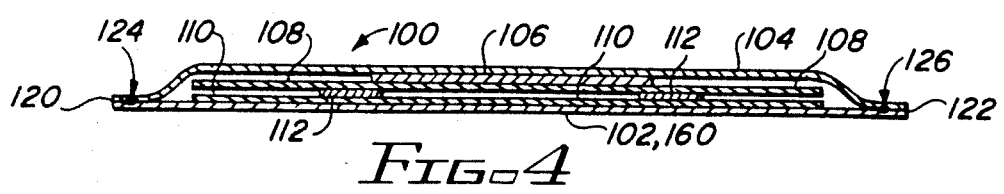
FIG. 4 is a schematic end elevation, in section, taken along the line 4—4 of FIG. 2 looking in the direction of the arrows.

The transfer sheet 106 is shown in the breakaway view of FIG. 2 as being immediately beneath the upper facing sheet 104. The breakaway at line A corresponds to a peeling away of the upper facing sheet 104, thereby exposing the transfer sheet 106 overlying the upper tissue layer 108. The breakaway at line B corresponds to the peeling away of the transfer sheet 106 and the upper tissue layer 108 in the corner of the pad below the line B. This displays one of the barrier strips 112 having an overlap with the transfer sheet 106 (shown between lines A and B). The lower tissue layer 110 is shown below the barrier strip 112. An optional second barrier strip 112A is indicated by broken line outline alongside the strip 112. The relative juxtaposition of the respective elements making up an underpad 100 may be clarified by reference to the end sectional view of FIG. 4.

Figure 5:
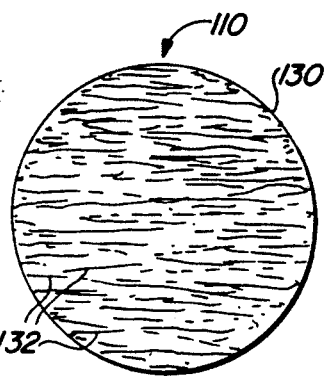
FIG. 5 is an enlarged schematic view of a portion of a component of the arrangement of FIG. 2.

The crepe construction of the tissue layers 108, 110 is represented in the enlarged schematic view of FIG. 5. This shows a portion 130 of one of the plies of the tissue layer 108 or 110 having an irregular, crepe-like surface with numerous surface irregularities 132 in the form of embossments and depressions. These are generally aligned in the transverse direction and are created by running the individual tissue plies in the transverse direction over a doctor blade configured to develop the crepe irregularities 132 of FIG. 5. As a consequence of this surface configuration, moisture which is absorbed in the tissue layers is directed by capillary action to migrate in the transverse direction of the pad 100 toward a barrier strip 112. Since the superabsorbent barrier strip readily soaks up any moisture which reaches it through the tissue layers 108, 110, a gradient wicking action in the tissue layers channels the liquid in the transverse direction toward the barrier strip 112 associated therewith.

Figure 6:
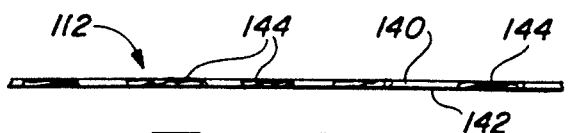
FIG. 6 is a schematic end view of a particular element in the arrangement of FIG. 2.

The construction of a barrier strip 112 is illustrated schematically in FIG. 6. As shown therein, the strip 112 comprises an upper layer 140 and a lower layer 142 which carry between them, generally randomly distributed throughout, a plurality of clumps 144 of superabsorbent powder. The strips 140, 142 with the powder between them are pressed together so as to serve as a carrier for the super-absorbent powder. Because of this structural configuration, the strips 112 effectively serve as a barrier to any liquid against passing a strip 112, at least until the strip 112 is fully saturated.

The second preferred embodiment of my invention as described hereinabove may be represented by the same drawing FIGS. 1-5 used to show the first embodiment, since the appearance as depicted is essentially the same. The difference resides in the backing layer 102 which for the second embodiment is designated 160. Instead of being impervious polypropylene as in the first embodiment, the backing layer is a heavier sheet of spun-bonded material, untreated with a surfactant such as that used in the upper facing sheet 104, which is permeable to air at an elevated pressure but resistant to the transfer of water. This finds application on air beds for burn patients, the elderly, etc.

Arrangements in accordance with the present invention are capable of absorbing a substantial quantity of liquid while still feeling dry to the touch and thus provide an effective underpad for the stated purpose. These pads have been found to be more effective than those which are known heretofore. A quantity of water equal to the contents of two coffee cups may be poured into the center of one of these pads and it will be totally absorbed within a very short time, leaving the surface of the upper facing layer essentially dry to the touch. This high liquid absorption capability is the result of the materials used, the components employed in the pad and the structural configuration of the respective elements.

This is a considerable improvement over pads over which use wood fiber fluff as the absorbent material, even when it is mixed with super-absorbent powder. In the fluff pads, the fibers are not connected and the water tends to puddle, sometimes interacting with the super-absorbent powder to develop a slime along the surface of the pad. The laminated barrier strips of the present pads prevent the water from going through, thereby eliminating the likelihood of hydraulic pressure from weight of the patient's body on the absorbent material forcing liquid through the backing layer to contaminate the air bed with which it is used.

Although there have been described hereinabove various specific arrangements of an underpad for incontinent patients in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An incontinence protection absorbent underpad for use on a supporting surface of an article of bedding comprising:
   a backing sheet which is impervious to liquid;
   an upper facing sheet which is permeable to liquid;
   means for adhering the upper facing sheet and the backing sheet together at the edges of the underpad;
   a liquid absorbent pad between the facing sheet and backing sheet for absorbing liquid which may be deposited on the facing sheet; and
   a transfer layer between the facing sheet and the liquid absorbent pad for transferring deposited liquid from the facing sheet to the pad while inhibiting the transfer of liquid in the opposite direction;
   wherein the liquid absorbent pad comprises upper and lower tissue layers generally coextensive with the edges of the pad and a plurality of spatially separated superabsorbent barrier strips situated between the tissue layers and extending generally parallel to the side edges of the underpad between the top and bottom edges of the pad, said strips being displaced from the central region of the pad;
   wherein each of the upper and lower tissue layers comprises a plurality of individual plies of highly absorbent tissue and is formed with creped surface irregularities with the surface irregularities being oriented in a transverse direction.

2. The underpad of claim 1 wherein the barrier strips are formed of laminated tissue layers having clumps of superabsorbent polymer powder distributed therein.

3. The underpad of claim 2 wherein the barrier strips are laminated of thin layers of tissue adhered together.

4. The underpad of claim 1 wherein the transfer layer is formed of non-woven polyester material.

5. The underpad of claim 1 wherein the upper facing sheet is formed of spun-bonded polypropylene with a sufficiently open fiber distribution to render it slightly transparent.

6. The underpad of claim 5 wherein the upper facing sheet is treated with a surfactant to improve its porosity for liquid.

7. The underpad of claim 4 wherein the backing sheet is formed of a continuous sheet of polypropylene plastic.

8. The underpad of claim 4 wherein the backing sheet is formed of a continuous layer of polyethylene.

9. The underpad of claim 1 wherein the surface irregularities of the tissue layers are oriented generally orthogonal to the barrier strips.

10. The underpad of claim 1 wherein said adhering means comprise a pair of glue lines extending along the side edges of the underpad approximately ½-inch in from the edges.

11. The underpad of claim 10 wherein said adhering means further comprise a layer of sprayed glue fibers extending generally along the top and bottom edges of the underpad covering a region extending to the terminal edges of the pad within the underpad.

12. The underpad of claim 5 wherein the backing sheet comprises a spun-bonded polypropylene layer of heavier material than the upper facing sheet, said backing sheet being permeable to air but generally impervious to liquid such as to admit air at an elevated pressure to the interior of the underpad from the underside.

13. An incontinent absorbent underpad for use in protecting bedding comprising:
   a plurality of absorbent tissue layers sandwiched between an impervious backing layer and a liquid permeable upper facing layer, the edges of the backing layer and the facing layer being adhered together along at least the side edges to contain liquid within the underpad; and
   a plurality of generally parallel superabsorbent barrier strips situated between upper and lower tissue layers, said strips being oriented generally parallel to the side edges of the underpad and positioned on opposite sides of the center of the underpad spaced from said side edges;
   said plurality of tissue layers comprising an upper tissue layer and a lower tissue layer respectively above and below said barrier strips, each of said tissue layers comprising a plurality of plies of highly absorbent tissue formed to provide a selectively directed capillary action for liquid absorbed therein.

14. The underpad of claim 13 wherein the direction of capillary action is from the center of the underpad outward toward the barrier strips and from the side edges inward toward the barrier strips.

15. The underpad of claim 13 further including means for selectively orienting the direction of capillary action provided by said tissue layer plies.

16. The underpad of claim 15 wherein said means comprise creped tissue plies with the crepe direction oriented transversely of the underpad.

17. The underpad of claim 13 further including a transfer layer located between the upper tissue layer and the upper facing layer, which transfer layer is formed to develop preferential directional transmissibility of liquid therethrough.

18. The underpad of claim 13 wherein said strips are two in number, each being formed of laminated tissue layers with clumps of super-absorbent powder distributed therein.

19. The underpad of claim 18 wherein each of said strips comprises a pair of thin absorbent tissue layers with the clumps of super-absorbent powder scattered throughout the strip and held between said layers.

20. The underpad of claim 13 wherein said strips are positioned in two pairs located on opposite sides of the center region of the underpad, each of said strips being formed of laminated tissue layers with clumps of super-absorbent powder distributed therein.

21. The underpad of claim 20 wherein each of said strips comprises a pair of thin absorbent tissue layers with the clumps of super-absorbent powder scattered throughout the strip and held between said layers.

22. The underpad of claim 13 wherein said backing layer comprises a sheet of plastic which is impervious to liquid.

23. The underpad of claim 13 wherein said backing layer comprises a spun-bonded layer of 1½ ounce weight material with a distribution of fibers such that the layer is permeable to air but highly resistant to the flow of liquid therethrough.

24. The underpad of claim 13 wherein the upper facing layer comprises spun-bonded polypropylene having an open fiber distribution layer treated with a surfactant to enhance its permeability to liquid.

* * * * *